United States Patent [19]
Tatsumi et al.

[11] Patent Number: 4,634,490
[45] Date of Patent: Jan. 6, 1987

[54] METHOD OF MONITORING SINGLE CRYSTAL DURING GROWTH

[75] Inventors: Masami Tatsumi; Shin-ichi Sawada; Ryusuke Nakai, all of Osaka, Japan

[73] Assignee: Sumitomo Electric Industries, Ltd., Osaka, Japan

[21] Appl. No.: 679,895

[22] Filed: Dec. 10, 1984

[30] Foreign Application Priority Data

Dec. 16, 1983 [JP] Japan ................................ 58-237669

[51] Int. Cl.⁴ ............................................. C30B 15/26
[52] U.S. Cl. ...................................... 156/601; 378/73
[58] Field of Search .................. 156/601; 422/108; 378/73

[56] References Cited

U.S. PATENT DOCUMENTS 3,105,901 10/1963 Ladell et al. ........................ 378/73
3,499,736 3/1970 Zwaneburg ........................ 156/601

FOREIGN PATENT DOCUMENTS 174598 10/1984 Japan ................................. 156/601

OTHER PUBLICATIONS

Van Dijk et al., Jl of Crystal Growth vol. 21, 1974 pp. 310–312.

Primary Examiner—Hiram H. Bernstein
Attorney, Agent, or Firm—Cushman, Darby & Cushman

[57] ABSTRACT

Single crystal during growth is irradiated by an slitted X-ray beam and the diffracted X-ray beam from the crystal is monitored by an image amplifier with a two dimensional manner so that the diffracted X-ray can be monitored by the image amplifier even if there occurs change of the diameter of the crystal. A half portion of the single crystal during growth is irradiated by a slitted X-ray beam and the other half portion of the crystal is irradiated by the X-ray beam over the entire height of the crystal so that the Laue spots of the crystal growth is displayed on one half portion of the display of the image amplifier and a shape of the crystal being pulled up is monitored in another half portion of the display of the image amplifier.

4 Claims, 9 Drawing Figures

METHOD OF MONITORING SINGLE CRYSTAL DURING GROWTH

FIELD OF THE INVENTION

The present invention relates to a method of monitoring a single crystal during growth, and more particularly to a monitoring method of a single crystal using a display system such as a CRT monitor or the like during growth of the crystal produced by a pulling up method or a floating melting accumulation method.

BACKGROUND OF THE INVENTION

There are proposed several methods of controlling the growth of the single crystal for use in semiconductors or optical devices by monitoring the state of the growth of the single crystal by irradiating X rays thereto. In one example, Japanese Patent Publication No. 34440/1973 discloses that as shown in FIG. 1, characteristic X-rays 6 are projected through a slit 2 from an X-ray source 1 to a single crystal 3 which is rotated around the pulling up axis with a constant rotating speed, then the X-rays 7 diffracted from the crystal plane of the single crystal is measured by a counter device such as a proportional counter or a scintillation counter, so that the growth of the single crystal is monitored, thereby controlling the rotational speed of the single crystal, calibrating the growth direction or observing the state of the crystal such as a fault of the crystal. In FIG. 1, the reference numeral 4 is a furnace body such as a quartz crucible and 5 is a crystaline material to be grown to the single crystal.

However, this proposed method has a disadvantage that it is very difficult to recognize the correct crystaline state since detection of the diffracted X-rays by the counter due to difficulty in correct geometric setting of the X-ray source, crystal and counter. More specifically, since the characteristic X-ray source is used with a fine opening of the slit 2, the width of the diffracted X-rays is very small and therefore can only be detected in the reflection angle of 2θ and furthermore, since the crystal is rotated, the reflection of the X-ray from the crystal is interrupted, whereby the counter can not surely detect the diffracted X-rays partly because the direction of the reflection of the X-ray is changed corresponding to the change of the diameter of the grown crystal and the finder of the scintillation counter is relatively small. Furthermore, according to the proposed method, since only the traces of the Laue spots of the crystal plane can be observed, change of the diameter of the crystal pulled up can not be detected, whereby control of the diameter of the pulled crystal can not be made by only monitoring the output of the scintillation counter.

While the JOURNAL OF CRYSTAL GROWTH 310–212 (1974) proposes another way of monitoring of the crystal growth wherein an X-ray image amplifier is used to monitor the crystal in a two dimensional manner by irradiating the white X-rays onto the crystal which is in the pull up process. However, this proposed way is only possible to recognize the change in the shape of the crystal and is impossible to recognize the crystal characteristic such as twin crystal or multiple crystal.

SUMMARY OF THE INVENTION

An essential object of the present invention is to provide a method of monitoring a single crystal during growth which enables not only to judge the crystalline characteristics in spite of rotation of the crystal during process of growing of single crystal but also to recognize the shape of the crystal without a precise geometrical setting of an X-ray sensor.

Another object of the present invention is to provide a method of monitoring the crystal growth which enables to visually recognize the crystal state instantly.

A still further object of the present invention is to provide a method of monitoring the crystal growth wherein various states of crystal such as occurrence of twin crystal and/or diameter of the pulled crystal can be observed in one display.

According to one aspect of the present invention there is provided a method of monitoring growth of a single crystal which is pulled up from melted crystal material, being rotated in a predetermined speed which includes a step of irradiating an X-ray beam on rising part of the pulled single crystal, a step of receiving white X-ray and characteristic X-ray diffracted by the crystal plane of the pulled up crystal by a monitoring means which is able to monitor the diffracted rays with a two dimensional area, so that the growth state of the crystal can be monitored by the monitoring means. Since the diffracted X-ray beam is received by a monitoring means of two dimensional manner, it is not necessary to adjust the positions of the crystal to be monitored and the monitoring means for receiving the diffracted X-ray, thereby facilitating to monitor the crystal growth.

Further more, the diffracted X-ray can be received by two dimensional monitoring means even if there occurs change of the diameter of the crystal growth, thus it makes possible to monitor the states of the crystal correctly without readjustment of the direction of the slit and the relative position between the crystal and the monitoring means as occurred in the prior art.

According to another aspect of the present invention, there is provided a method of monitoring growth of a single crystal which is pulled up from melted crystal material, being rotated in a predetermined speed which includes a step of irradiating a X-ray beam on an entire height of one half portion of the pulled crystal and irradiating a slitted X-ray beam on a rising portion of another half portion of the pulled crystal, a step of receiving white X-ray and characteristic X-ray diffracted by the crystal plane of the pulled up crystal by a monitoring means which is able to monitor the diffracted rays with a two dimensional area and displaying a shape of said one half portion of the pulled crystal in a half portion of a display portion of the monitoring means and Laue spots of another half portion of the rising part of the pulled up crystal in another half portion of the display portion of the monitoring means.

According to the aspect of the present invention as described above, since the shape of the crystal growth and the Laue spots can be displayed in one display at a time so that change of the appearance of the pulled crystal such as a diameter of the crystal and the presence of twin crystal can be observed in one display at a time.

DETAILED DESCRIPTION OF A PREFERRED EMBODIMENT

Figure 1:
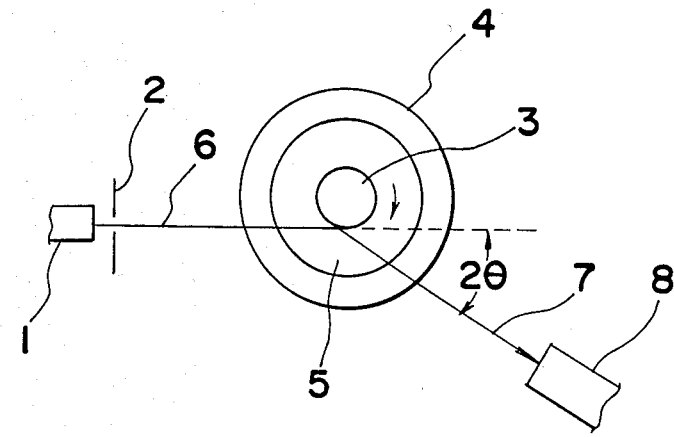
FIG. 1 is a schematic diagram showing one example of arrangement of the conventional system for monitoring the crystal growth.
Figure 2:
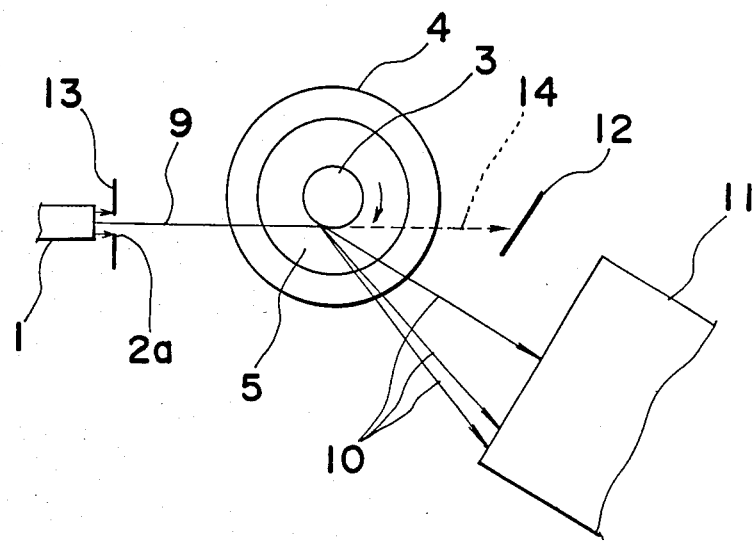
FIG. 2 is a schematic plan view of a monitoring system according to the present invention.

Referring to FIG. 2, X-rays radiated from an X-ray source 1 are passed through a slit 2a having an opening horizontally elongated but narrow in the vertical direction and the X-rays are formed into a strip like X-ray beam 9 having a predetermined horizontal width. Said x-ray beam 9 is irradiated onto a peripheral edge portion of the rotating crystal 3 to be grown into the single crystal on the portion just rising from the crystal material in the quartz crucible 4 so that a Bragg reflection wave including a white X-ray beam and a characteristic X-ray beam 10 can be reflected from the rising portion of the pulled single crystal 3. Shielding plate 12 prevents X-rays 14 which pass by crystal 3 from entering image amplifier 11. The white X-ray beam and the characteristic X-ray beam 10 are respectively received by an image amplifier 11. The image amplifier 11 comprises a fluorescent plate with a predetermined two dimensional area and a television system having a camera to scan the fluorescent plane and a CRT (cathode ray tube) display device for visually displaying the video signal obtained from the camera to monitor the image depicted on the fluorescent plate.

In this arrangement, the image amplifier 11 displays one or more the Laue spots of the single crystal thus pulled up from the crystal material. In place of the image amplifier 11, various device which is able to observe the state of the crystal by using the diffracted pattern of the crystal using the two dimensional white X-ray, characteristic X-ray may be used. For examples, a plurality of NaI scintillation counters arranged to detect the crystal in the two dimensional manner, or a solid state image pick up device or a photograph may be used.

Figure 3A:
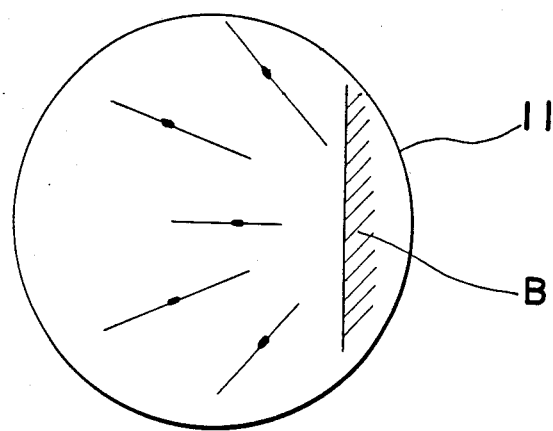
FIGS. 3(a), 3(b) and 3(c) are front views showing examples of displayed pattern of the traces of the Laue spots monitored by the method according to the system shown in FIG. 2 when single crystal is monitored.
Figure 3B:
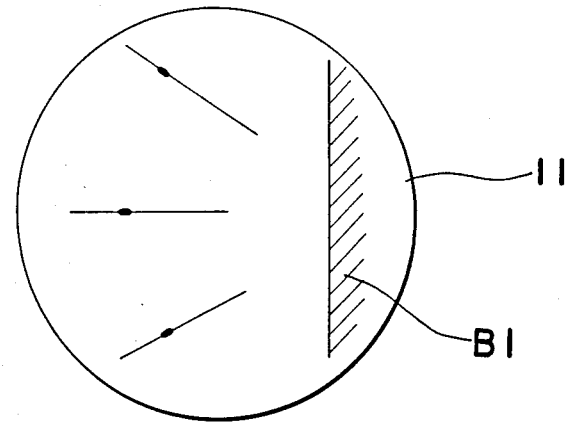
Figure 3C:
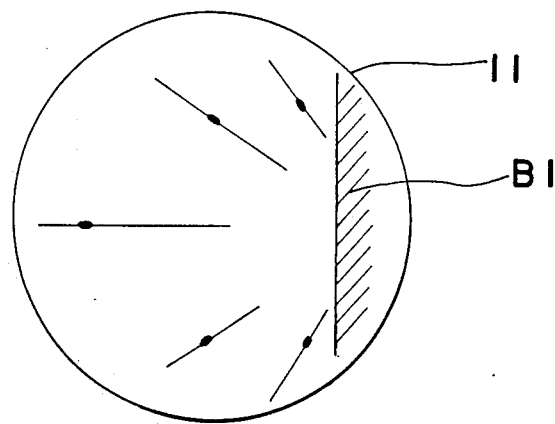
Figure 4A:
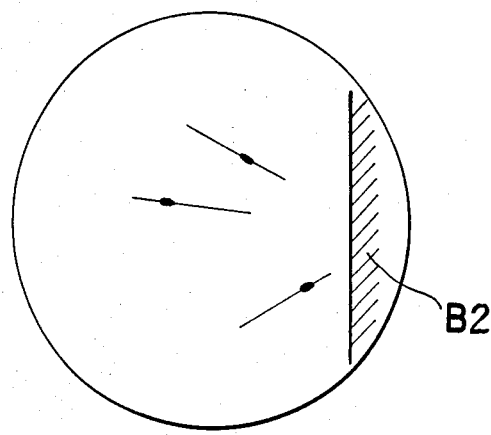
FIGS. 4(a) and 4(b) are front views showing examples of displayed pattern of the traces of the Laue spots monitored by the method of the system shown in FIG. 2 when twin crystal is monitored.
Figure 4B:
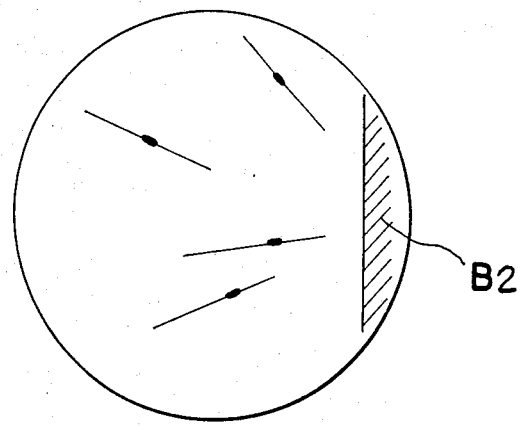

In the arrangement shown in FIG. 2, a position adjustment is made to catch the Laue spots near the low angle ($2\theta$ 10° through 20°) coming from the InP single crystal in the growing process. In order to improve the S/N ratio, the image amplifier 11 is shielded with a lead plate so as to prevent entrance of undesired X-rays such as leaked X-rays into the image amplifier 11. The Laue spots of the characteristic X-ray monitored on the image amplifier 11 are displayed on the CRT display of the image amplifier 11, being turned on and off periodically according to the rotation of the single crystal 3 and the Laue spots of the white X-ray monitored on the CRT display of the image amplifier 11 are moved towards the center of the display device of the image amplifier 11. As shown in FIG. 3, in case of the single crystal, there can be observed on the CRT display of the image amplifier 11 the diffraction pattern of the white X-ray and the characteristic X-ray each extending in the radial direction with the upper half and the lower half of the displayed patterns to be symmetrical. When the twin crystal is formed in the crystal, asymmetrical pattern deviated from the symmetry of single crystal as shown in FIG. 4 can be observed. In FIGS. 3 and 4, B1 shows the image of the InP single crystal and B2 shows the image of the InP twin crystal. Therefore, by recognizing the patterns on the CRT display, the characteristics of the crystal such as the poly crystal and the presence of the twin crystal and so on can be classified.

Figure 6:
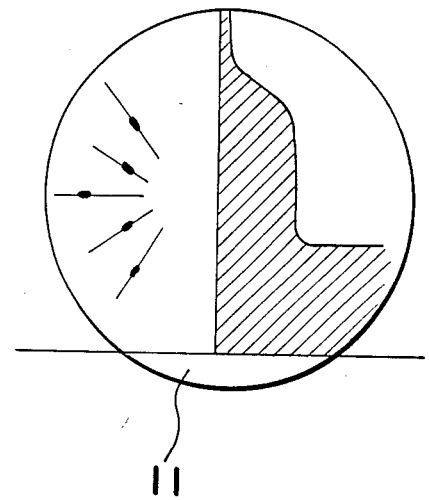
FIG. 6 is a schematic front view showing an example of displayed pattern of the crystal monitored by the system shown in FIG. 5.
Figure 5:
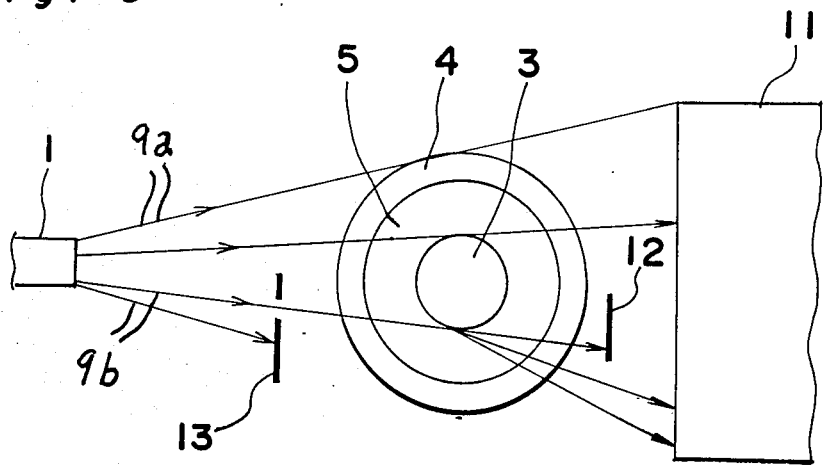
FIG. 5 is a schematic plan view of another monitoring system according to the present invention.

Referring to FIG. 5, which shows another example of the method of monitoring the crystal growth according to the present invention, the right half 9a (as viewed from detector 11) of the the X-rays of the X-ray source 1 are directly entered on the entire height of the right half portion of the pulled single crystal 3 which is being pulled from the crystal material in crucible 4. On the contrary, there is disposed a slit 13 having a horizontal elongated opening in the left half X-ray portion 9b between the X-ray source 1 and the pulled single crystal 3 so that a strip like X-ray beam extending horizontally with a thin thickness can be irradiated onto the left half of the rising portion of the single crystal. In the example, the horizontal length of the opening of the slit 13 is 10 through 20 mm and the vertical width thereof is 1 through 3mm, the distance between the X-ray source 1 and the crystal is about 700 mm and the distance between the crystal and the detector 11 is 300 mm. By this arrangement, since the X-rays are irradiated on the entire height of the right half portion of the pulled single crystal 3, a shape of the right half portion of the pulled single crystal which is being pulled up can be displayed on the one half portion, for example on the right half portion of the CRT display of the detector 11 as shown in the right half portion of FIG. 6, whereby the states of the pulled single crystal 3 such as change of the diameter thereof can be directly monitored. In addition since the slitted X-ray beam is irradiated onto the rising part of the left half portion of the pulled single crystal 3, the traces of the Laue spots due to the Bragg reflected wave can be displayed on another half portion, for example on the left half portion of the CRT display of the image amplifier 11 as shown in the left half portion of FIG. 6, whereby it can be judged whether or not there occurs the twin crystal or disturbance or destroy of the crystal.

It is therefore possible to monitor all of the characteristics and the states of the crystal growth by the CRT display on the image amplifier.

By monitoring the characteristics and the states of the crystal displayed on the image amplifier 11, the conditions of production of the single crystal such as, temperature of the furnace, rotational speed of the crystal or pull up speed can be controlled by the operator so as to produce the desired single crystal.

What is claimed is:

1. A method of monitoring growth of a single crystal which is pulled up from melted crystal material, being rotated at a predetermined speed which includes a step of passing an X-ray beam through a slit elongated in the horizontal direction with a small vertical width, a step of irradiating the slitted X-ray beam on the rising part of the pulled single crystal, a step of receiving white X-ray and characteristic X-ray diffracted by the crystal plane of the pulled up crystal by a monitoring means for displaying one or more patterns in a two dimensional area to show the crystal lattice structure of the growing crystal.

2. The method according to claim 1, wherein said monitoring means is an image amplifier comprising a fluorescent plate with a predetermined area for receiving the diffracted characteristic X-ray and the white X-ray and a television system for visually displaying the pattern on appearing on the fluorescent plate.

3. A method of monitoring growth of a single crystal which is pulled up from a melted crystal material, being rotated at a predetermined speed which includes a step of irradiating an X-ray beam on an entire height of one half portion of the pulled crystal and irradiating a slitted X-ray beam on a rising portion of another half portion of the pulled crystal, a step of receiving white X-ray and characteristic X-ray diffracted by the crystal plane of the pulled up crystal by a monitoring means which is able to monitor the diffracted rays with a two dimensional area and displaying a shape of said one half portion of the pulled crystal in a half portion of a display portion of the monitoring means and two dimensional patterns showing the crystal lattice structure of another half portion of the rising part of the pulled up crystal in another half portion of the display portion of the monitoring means.

4. The method according to claim 3, wherein said monitoring means is an image amplifier comprising a fluorescent plate with a predetermined area for receiving the diffracted characteristic X-ray and the white X-ray and a television system for visually displaying the pattern on appearing on the fluorescent plate.

* * * * *